(12) United States Patent
Coker et al.

(10) Patent No.: US 6,582,607 B2
(45) Date of Patent: Jun. 24, 2003

(54) METHOD OF DEWATERING ORGANIC LIQUIDS

(75) Inventors: Eric Nicholas Coker, Albuquerque, NM (US); Richard Duncan Oldroyd, Tonbridge (GB); Warren John Smith, Feltham (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/873,317

(22) Filed: Jun. 5, 2001

(65) Prior Publication Data

US 2002/0014457 A1 Feb. 7, 2002

Related U.S. Application Data

(63) Continuation of application No. PCT/GB99/03881, filed on Sep. 14, 2000.

(30) Foreign Application Priority Data

Dec. 10, 1998 (GB) .............................................. 9827099
Mar. 3, 1999 (GB) .............................................. 9904910
Mar. 18, 1999 (GB) .............................................. 9906298

(51) Int. Cl.$^7$ .......................... B01D 65/00; B01D 15/04
(52) U.S. Cl. ....................... 210/639; 210/644; 210/689; 210/770; 502/85; 568/916
(58) Field of Search ................................ 210/634, 638, 210/639, 644, 689, 770; 568/916, 917; 549/429; 502/85

(56) References Cited

U.S. PATENT DOCUMENTS

| 4,130,484 A | * | 12/1978 | Marwil et al. ............... 568/917 |
| 4,319,057 A | * | 3/1982 | Kiser ......................... 568/916 |
| 4,460,476 A | * | 7/1984 | McCaffrey et al. ......... 210/689 |
| 4,726,818 A | * | 2/1988 | Yeung et al. ................ 210/689 |
| 4,894,142 A | * | 1/1990 | Steigleder .................... 502/85 |
| 5,143,878 A | * | 9/1992 | Dai et al. |
| 5,316,656 A | * | 5/1994 | Pellet et al. |
| 5,504,259 A | | 4/1996 | Diebold et al. |

FOREIGN PATENT DOCUMENTS

GB 2 088 739 A 6/1982

* cited by examiner

Primary Examiner—Joseph Drodge
(74) Attorney, Agent, or Firm—Nixon & Vanderhye

(57) ABSTRACT

Process for dewatering organic liquids admixed with water wherein the admixture is brought into contact with a molecular sieve. The moleculat sieve is pretreated so as to reduce its acid site concentration and attain an ammonia TPD value of 18 mmol/g or less prior to contact with the admixture. The present invention relates to a process for dewatering organic liquids admixed with water, said process comprising bringing the admixture into contact with a molecular sieve, characterized in that the molecular sieve is pretreated so as to reduce its acid site concentration and attain an ammonia TPD value of 18 mmol/g or less prior to contact with the admixture.

19 Claims, No Drawings

METHOD OF DEWATERING ORGANIC LIQUIDS

This application is a continuation of PCT/GB99/03881 filed Sep. 14, 2000.

The present invention relates to a method of dewatering organic liquids, especially alcohols, using a molecular sieve which has been pretreated to absorb the water therefrom.

Alcohols and esters are usually produced in an environment containing water or moisture, be it as a reactant during hydration of olefins to form the alcohol or as a by product of a condensation reaction between a carboxylic acid and an alcohol to form the ester. The product alcohol and ester are usually contaminated inter alia with water. More, specifically where a synthetic route is used to produce an alcohol such as ethanol or isopropanol by the hydration of an olefin such as ethylene or propylene respectively, water is a reactant and hence it is inevitable that the product is contaminated with water. Again, alcohols produced by the biofermentation routes from agricultural feedstocks such as corn, beet and sugarcane, and by processing of biomass such as agricultural residues, herbaceous crops, waste paper and pulp, or municipal wastes are also contaminated with water. More importantly, methods of removing water from such products are complicated by the fact that in the case of ethanol, for instance, it forms an azeotrope with water thereby making the dewatering thereof difficult. Cumbersome and expensive methods have to be used. Of the various methods suggested for dewatering aqueous alcohols, the following processes may be considered typical: use of ion-exchange resins (DE-A-4118156), pervaporation using membranes (JP-A-04308543); treatment with an ortho-ester and followed by passing through a set of catalyst beds (DD-A-278336); by reaction with 2,2-dialkoxy-propane on a catalyst bed comprising acid ion-exchange resin and an acid zeolite (DD-265139); selective extraction of ethanol in the mixture into liquid carbon dioxide (EP-A-231072); using a combination of extraction with liquid carbon dioxide and a molecular sieve and then fractional distillation (EP-A-233692); azeotropic distillation in the presence of an entrainer such as eg cyclohexane; and, of course, the use of various types of molecular sieves or zeolites (EP-A-205582, GB-A-2151501, EP-A-142157, EP-A-158754, U.S. Pat. No. 4,407,662, U.S. Pat. No. 4,372,857, GB-A-2088739 and FR-A-2719039). The use of molecular sieves is an attractive method because of its relatively simplicity and low cost. In the last-named FR-A-2719039, the principle feature is the use of a super-heated, partially dried alcohol to regenerate the used molecular sieve.

One of the problems associated with the use of conventional molecular sieves is that by-products are usually formed due, e.g. to the reversal of the olefin hydration reaction, i.e. back conversion of isopropanol to propylene and water, or the hydrolysis of an ester back to the reactant alcohol and carboxylic acid, thereby resulting in the loss not only of the valuable product but also the chemicals, effort and energy expended in the first place in the hydration and esterification reactions respectively.

It has now been found that the cause of this reversal and the consequent loss of purity can be avoided if the molecular sieves are pretreated according to the invention prior to contact with the aqueous organic liquids.

Accordingly, the present invention is a process for dewatering organic liquids admixed with water, said process comprising bringing the admixture into contact with a molecular sieve, characterised in that the molecular sieve is pretreated so as to reduce its acid site concentration and attain an ammonia TPD value of 18 $\mu$mol/g or less prior to contact with the admixture.

By "molecular sieve" is meant here and throughout the specification the sieve as such or when such sieve is bound in or with a binder.

By "ammonia TPD value" is meant here and throughout the specification, an ammonia temperature desorption value which is the amount of ammonia desorbed from a molecular sieve after said sieve has been fully saturated with ammonia and then subjected to a thermal desorption until no more ammonia is evolved. As such the "ammonia TPD value" represents the concentration of acid sites in the molecular sieve accessible to ammonia. The acid site concentration can of course be defined by other well known characterisation techniques such as infrared spectroscopy and microcalorimetry. The ammonia TPD value of the molecular sieves used in the present invention for dewatering is suitably determined by initially heating a preweighed amount of a commercial sample of a molecular sieve to an elevated temperature e.g. about 150° C., at the rate of about 10° C. per minute in an inert atmosphere, then reducing the temperature of the heated sieve to about 100° C. in an inert atmosphere over an extended period, eg overnight at that temperature, and then re-heating the ammonia saturated sieve to about 700° C. at the rate of 10° C. per minute and measuring the amount of ammonia desorbed from the molecular sieve. Determination of the desorbed ammonia can be carried out by titration of the desorbed gases using a dilute mineral acid solution such as e.g. 0.02N hydrochloric acid.

In the case of commercially available molecular sieves which are in the so called "potassium cation form", the ammonia TPD value is generally greater than 19 $\mu$mol/g and is typically in the range from 19 to 25 $\mu$mol/g. However, after pretreatment, the ammonia TPD value of the treated molecular sieve is $\leq$18 $\mu$mol/g, suitably less than 15 $\mu$mol/g and preferably less than 12 $\mu$mol/g, eg from 1–11.5 $\mu$mol/g.

Molecular sieves which are capable of adsorbing the water from an admixture thereof with an alcohol are well known. Typically, such molecular sieves are crystalline although the particular sieve employed is not critical. Such sieves should, however, be capable of adsorbing at least 2% by weight of water, e.g. from 2–30% w/w, preferably from about 5–25% w/w under the adsorption conditions. The sieve is suitably a zeolitic molecular sieve having an average pore diameter of about 3 Angstroms (Å). Typical examples of such molecular sieves are the A type zeolites, especially 3A, although others having different pore diameters such as eg 4A and 5A may also be used. Almost all commercially available molecular sieves which have hitherto been used in the dewatering process especially of alcohols though sold as a "potassium cation form" invariably have an ammonia TPD value of greater than 19 $\mu$mol/g. Typical examples of such commercially available zeolitic molecular sieves are those sold as UOP AS-5078 and Ceca Siliporite® NK30 although such molecular sieves are also available from other sources. These, so-called "potassium cation forms" as described e.g. in EP-A-0 142 157, when used as such for dewatering( aqueous alcohols result in a significant amount of by products formation such as e.g. olefins, ethers and/or aldehydes. This is unacceptable for the by-products may not only contaminate the solvent alcohol being treated but may also undergo further degradation or polymerisation in the presence of the untreated molecular sieve thereby further adversely affecting the quality of the dewatered alcohol and the consequent loss of alcohol purity. That this is the case can be seen e.g. from the description at column 2, lines 50–60 of U.S. Pat. No. 4,460,476 referred to above and also from the examples and comparative tests shown below.

The feature of the present invention is that such so-called "potassium cation form" of zeolitic molecular sieves can be further treated to reduce the ammonia TPD value thereof to the levels now claimed prior to contact with the organic liquid-water admixture in order to carry out the dewatering process. The further treatment is suitably carried out by bringing the commercially available molecular sieve into contact with a solution of an ammonium or an alkali metal salt, such as e.g. a salt of sodium or potassium, especially e.g., the nitrate salt to enable any residual $H^+$ cations in the commercial sieve to be exchanged with the additional alkali metal cations. A final washing procedure is then carried out to remove any residual salt and acids produced as a result of the ion exchange procedure. The alkali metal salt is suitably used as an aqueous solution and the concentration of the aqueous solution of the ammonium or alkali metal salt used will depend upon the nature of the untreated molecular sieve. Typically, however, such concentration is suitably in the range from about 0.01 to 2 molar, preferably from about 0.05 to 0.5 molar. The treatment of the untreated molecular sieve is suitably carried out at a temperature in the range from 10 to 90° C., preferably from 20 to 70° C. By this method the ammonia TPD value of the commercial molecular sieve such as 3A can be reduced to values of 18 $\mu$mol/g or below, suitably below 15 $\mu$mol/g and preferably below 12 $\mu$mol/g. Usually, the ammonia TPD value of the untreated molecular sieve is reduced by at least 10%, preferably by at least 40% prior to use in the dewatering method of the present invention. Alternatively, the aforementioned treatment can be carried out on any binder used in the preparation of the bound molecular sieve prior to the sieve beings bound in or with the binder. In this instance, the treatment should be carried out to the extent that the ammonia TPD value of the final bound molecular sieve is within the ranges specified above. Typical binders used in bound molecular sieves are montmorillonites, kaolin, sepiolites and atapulgites In the dewatering process, the molecular sieve of reduced ammonia TPD value is brought into contact with the organic liquid-water admixture to be dewatered. This may be done batchwise or continuously e.g. by packing a column with an amount of the substantially acid-free molecular sieve and then passing the admixture to be dewatered therethrough. The rate of passage of the admixture to be dewatered through the packed column is suitably such that there is adequate contact time between the admixture and the sieve. Such contact time would of course depend upon a. the nature of the organic liquid in the admixture,
b. the amount of water in the admixture,
c. the capacity of the molecular sieve used,
d. the temperature and pressure at which the two are brought into contact, and
e. whether the admixture is in the liquid or in the gaseous phase.

Typically, however, such contact time is suitably in the range from 15 seconds to 5 minutes for a unit volume of the admixture to pass through a unit volume of the molecular sieve. Within this range, if the admixture is e.g. a liquid mixture of water and isopropanol and it is passed through a pre-treated crystalline 3A molecular sieve at a temperature of say about 110–120° C., then such contact time would be in the range from about 30 seconds to 3 minutes, e.g. about 1 minute for a unit volume of the admixture to pass through a unit volume of the treated molecular sieve. By operating this process, an organic liquid substantially free of water can be recovered from the base of such a column assuming that the admixture to be dewatered is being fed into the top of the packed column.

Depending upon the efficiency of the molecular sieve, the used sieve which may be saturated with water can be regenerated i.e. the adsorbed water desorbed, either by the techniques of temperature swing desorption or pressure swing desorption. In the temperature swing method, a stream of hot fluid is passed through the used molecular sieve so as to drive the adsorbed water out of the sieve. For a given pressure, the quantity of water adsorbed diminishes with increasing temperature. In the pressure swing method, desorption of the adsorbed water can be achieved by significantly reducing the pressure relative to that under which adsorption was carried out.

The efficiency of the dewatering process can be improved by operating two columns simultaneously such that when one of the columns is in the adsorption mode the other is in the desorption mode and the feed of the admixture to be treated is passed through the column in the adsorption mode thereby enabling a substantially continuous operation.

The process is particularly suitable for use in dewatering alcohols such as e.g. ethanol, isopropanol, secondary butanol and tertiary butanol, and aliphatic esters such as e.g. n-propyl formate, ethyl acetate, butyl acetate, methyl propionate and ethyl isobutyrate whether they be produced by a synthetic route such as e.g. alcohols produced by olefin hydration processes or whether they be produced by the biofermentation of agricultural feedstocks such as corn, beets and molasses, the latter process including alcohols, especially ethanol/water mixtures, produced by the processing of Biomass such as agricultural residues, herbaceous crops, waste paper and pulp, and municipal solid wastes.

The present invention is further illustrated with reference to the following Examples and Comparative Tests (not according to the invention):

EXAMPLES

In the Examples and Comparative Tests, two commercial grades of potassium ion-exchanged molecular sieves (zeolite 3A) were tested, namely UOP AS-5078 (ex, Universal Oil Products) and Ceca Siliporite® NK30 (ex, Ceca) which are both sieves which were already bound with a binder.

A. Treatment of Molecular Sieve

The following procedure was used for treating these commercially available molecular sieves with further amounts of alkali metal salts in order to reduce the acidity of these commercial samples:

An aqueous solution of potassium nitrate (0.1 M) was prepared by dissolving potassium nitrate (2.05 g, ex Sigma Aldrich) in distilled water (200 ml). The resultant potassium nitrate solution was poured into a container holding zeolite 3A molecular sieve (75 g). The container was sealed and agitated periodically over 20 hours at ambient temperature. The resultant potassium ion-exchanged molecular sieves were filtered, washed three times with further aliquots of distilled water (200 ml each) and dried in an oven at 140° C. These potassium ion-exchanged molecular sieves were then crushed and sieved to an average particle size of about 0.5–0.85 mm for use in the dewatering test rig.

B. Ammonia Temperature Programmed Desorption Experiments

A sample (300 mg) of an untreated commercial molecular sieve was accurately weighed into a quartz U-tube and attached to the ammonia TPD apparatus. The sample was heated to 150° C. at a rate of 10° C. per minute in flowing nitrogen and held at 150° C. for one hour. The temperature was then reduced to 100° C. and the sample saturated with ammonia using a 1% ammonia in nitrogen stream. After flushing with nitrogen overnight at 100° C., the sample was heated to 700° C. at the rate of 10° C. per minute. The desorbed ammonia was continuously titrated using 0.02 N hydrochloric acid.

One fresh sample of each of UOP AS-5078 and Ceca Siliporite® NK-30 sieve was subjected to a potassium ion exchange procedure (as outlined in Section A above). Each sample was then separately subjected to two further exchanges with potassium ions in an analogous fashion to give "triply exchanged" sieves.

The total amount of ammonia desorbed from each of the fresh and the "triply exchanged" sieves are shown below in Table 1. The triply exchanged sieves had an ammonia adsorption capacity of only 55% of that of the fresh (untreated) UOP sample and only 48% of that of the fresh (untreated) Ceca sample.

TABLE 1

| Total ammonia desorbed from molecular sieves at 700° C. | |
| --- | --- |
| Fresh UOP AS-5078 | 20.7 μmol/g |
| Triply Exchanged UOP AS-5078 | 11.4 μmol/g |
| Fresh Ceca Siliporite ® NK30 | 19.6 μmol/g |
| Triply Exchanged Ceca Siliporite ® NK30 | 9.5 μmol/g |

C. Dewatering Tests
(a) - Isopropanol

The dewatering test was carried out as follows: An adsorbent bed consisting of 30 ml of the potassium ion-exchanged molecular sieve from step (A) above was loaded into a glass reactor, followed by 5 ml of fused alumina beads for use as an inert pre-heater bed, the latter being separated from the adsorbent bed by a small amount of glass wool.

The charged glass reactor was fixed in place, and heated to 300° C. for 16 hours under a flowing stream of nitrogen (50 ml/minute). The adsorbent bed was then cooled to 120° C. and the rate of flow of nitrogen reduced to 25 ml/minute. A model azeotropic isopropanol mixture containing 88% w/w isopropanol and 12% w/w distilled water was passed over the adsorbent bed at a liquid flow rate of 2 ml/hour. A collection vessel (maintained at ambient temperature) was located downstream of the reactor to collect the dewatered (dried) liquid. A gas sample point was positioned downstream of the collection vessel. The gas emerging downstream from the collection vessel was analysed at regular intervals using a gas chromatogram fitted with an alumina KCI PLOT capillary column. Decomposition of isopropanol while passing over the potassium ion-exchanged molecular sieve is indicated by the presence of propylene in the exit gas stream downstream of the collection vessel. Liquid samples were collected, weighed and analysed using a gas chromatogram fitted with a Poropak® S packed column. The analysis of the collected liquid samples showed that the water had been selectively adsorbed. GC analyses found no other detectable products in the condensed liquid samples. The tests were stopped before water broke through the adsorbent bed.

The results of the molecular sieves tested in both its forms, i.e. fresh, commercially sold (not according to the invention) and after potassium ion-exchange according to the invention are tabulated below (Table 2):

TABLE 2

| Observed Propylene concentration (ppm) in Exit Gas Streams | | | | |
| --- | --- | --- | --- | --- |
| Time on | UOP AS-5078 | | Ceca Siliporite ® NK30 | |
| Stream (hrs) | Fresh* | Treated | Fresh* | Treated |
| 0.00 | | | | |
| 0.10 | 1.94 | | | 0.00 |
| 0.17 | | 0.00 | | |
| 0.33 | 1.01 | | | |
| 0.35 | | | 1.52 | 0.00 |
| 0.60 | | 0.00 | | |
| 0.73 | 0.67 | | 0.69 | |
| 1.02 | 0.40 | | 0.86 | 0.00 |
| 1.25 | 0.74 | | | |
| 1.38 | | 0.00 | | |
| 1.50 | 0.39 | | | |
| 1.55 | | | 0.38 | |
| 1.73 | 0.43 | | | |
| 2.00 | 0.00 | | | |
| 2.25 | 0.00 | | 0.32 | 0.00 |
| 2.72 | | 0.00 | | |
| 3.07 | 0.00 | | 0.43 | |
| 3.27 | | | | |
| 3.67 | 0.00 | | 0.34 | |
| 4.17 | 0.00 | | 0.22 | |
| 4.63 | | | 0.27 | |
| 5.48 | | | 0.29 | |
| 6.85 | | | 0.23 | 0.00 |
| 9.38 | | | 0.17 | |

*Comparative Tests, not according to the invention.

The above results show clearly that the decomposition of isopropanol to propylene during dewatering over commercially available molecular sieves is dramatically reduced when the sieves have been subjected to a prior potassium ion-exchange treatment.

(b)—Ethanol

The dewatering test was carried out as follows: an adsorbent bed consisting of 30 ml of either UOP AS-5078 molecular sieve or the same sieve after potassium ion-exchange treatment by the route described in step (A) above was loaded into a glass reactor, followed by 15 ml of fused alumina beads for use as an inert pre-heater bed, the latter being separated from the adsorbent bed by a small amount of glass wool.

The charged glass reactor was fixed in place, and heated to 350° C. for 16 hours under a flowing stream of nitrogen (50 ml/minute). The adsorbent bed was then cooled to 155° C. and the rate of flow of nitrogen reduced to 10 ml/minute. A model azeotropic ethanol mixture containing 94.4% w/w ethanol and 5.6% w/w distilled water was passed over the adsorbent bed at a liquid flow rate of 2 ml/hour. A collection vessel (cooled using an ice-bath) was located downstream of the reactor to collect the dewatered (dried) liquid. The collected liquid samples were weighed and analysed for diethyl ether using a gas chromatogram fitted with a CP Wax-57 CB capillary column. Karl-Fischer titrimetric analysis of the collected liquid samples showed that water had been adsorbed. The tests were stopped before water broke through the adsorbent bed.

The results of the molecular sieves tested in both its forms, ie fresh, commercially sold (not according to the invention) and after potassium ion-exchange treatment according to the invention are tabulated below (Table 3):

TABLE 3

Observed diethyl ether concentration (ppm) in dried liquid

| Time on Stream (min) | Unmodified UOP AS-5078 | Treated UOP AS-5078 |
|---|---|---|
| 180 | 76 | 4 |
| 240 | 77 | 5 |
| 300 | 79 | 7 |
| 360 | 69 | 8 |
| Water content of dried liquid | <0.27% w/w | <0.31% w/w |

The above results show clearly that the formation of diethyl ether during dewatering over commercially available molecular sieves is dramatically reduced when the sieves have been subjected to a prior potassium ion-exchange treatment.

We claim:

1. A process for dewatering organic liquids admixed with water, said process comprising bringing the admixture into contact with a molecular sieve, wherein the molecular sieve is pretreated so as to reduce its acid site concentration and attain an ammonia TPD value of 18 $\mu$mol/g or less prior to contact with the admixture.

2. A process as claimed in claim 1, wherein said molecular sieve is pretreated so as to reduce its acid site concentration and attain an ammonia TPD value of 1–11.5 $\mu$mol/g.

3. A process as claimed in claim 1, wherein said molecular sieve is a zeolitic molecular sieve having an average pore diameter of about 3 Angstroms (Å).

4. A process as claimed in claim 1, wherein said molecular sieve is in a potassium cation form.

5. A process as claimed in claim 1, wherein said pretreatment is carried out by bringing said molecular sieve into contact with a solution of an ammonium or an alkali metal salt.

6. A process as claimed in claim 5, wherein said pretreatment is carried out by bringing said molecular sieve into contact with a solution of an ammonium or an alkali metal salt having a concentration of 0.01 to 2 molar.

7. A process as claimed in claim 1, wherein said pretreatment is carried out by bringing said molecular sieve into contact with a solution of sodium nitrate or potassium nitrate.

8. A process as claimed in claim 1, wherein said pretreatment is carried out at a temperature of 10 to 90° C.

9. A process as claimed in claim 1, wherein said pretreatment causes the TPD value of the molecular sieve to be reduced by at least 40%.

10. A process as claimed in claim 1, wherein said molecular sieve is bound by a binder.

11. A process as claimed in claim 10, wherein said molecular sieve is bound by a binder formed of montmorillonite, kaolin, sepiolite or attapulgite.

12. A process as claimed in claim 1, wherein after said pretreatment step, said admixture is brought into contact with the pretreated molecular sieve by packing a column with an amount of said pretreated molecular sieve, and then passing said admixture therethrough.

13. A process as claimed in claim 1, wherein after said pretreatment step, said admixture is brought into contact with the pretreated molecular sieve at a temperature of 110–120° C. by packing a column with an amount of said pretreated molecular sieve, and then passing said admixture therethrough.

14. A process as claimed in claim 1, which further comprises the step of regenerating the molecular sieve after said molecular sieve is contacted with said admixture.

15. A process as claimed in claim 14, wherein said regeneration step is carried out by temperature swing desorption or pressure swing desorption.

16. A process as claimed in claim 1, wherein said organic liquid comprises an alcohol.

17. A process as claimed in claim 16, wherein said alcohol is selected from the group consisting of: ethanol, isopropanol, secondary butanol and tertiary butanol.

18. A process as claimed in claim 1, wherein said organic liquid comprises an ester.

19. A process as claimed in claim 18, wherein said ester is selected from the group consisting of: n-propyl formate, ethyl acetate, butyl acetate, methyl propionate and ethyl isobutyrate.

* * * * *